(12) United States Patent
Lukas et al.

(10) Patent No.: US 6,766,548 B1
(45) Date of Patent: Jul. 27, 2004

(54) ACCESSORIES MOUNT FOR AN ELECTRIC TOOTHBRUSH

(75) Inventors: Andrea Lukas, Offenbach (DE); Harald Trocha, Offenbach (DE)

(73) Assignee: Rowenta-Werke GmbH (DE)

( * ) Notice: Subject to any disclaimer, the term of this patent is extended or adjusted under 35 U.S.C. 154(b) by 356 days.

(21) Appl. No.: 09/629,607

(22) Filed: Jul. 31, 2000

(30) Foreign Application Priority Data

Jul. 31, 1999 (DE) .................................... 299 13 406 U

(51) Int. Cl.[7] .......................... A61C 17/22; A61C 15/04
(52) U.S. Cl. ..................... 15/22.1; 132/322; 433/118; 433/122; 601/142
(58) Field of Search ............................. 15/22.1, 176.4, 15/176.5; 132/322; 433/118, 119, 122, 123; 601/142; 606/161

(56) References Cited

U.S. PATENT DOCUMENTS

| | | | | |
|---|---|---|---|---|
| 1,414,886 A | * | 5/1922 | Matsunaga | ................. 15/176.4 |
| 4,880,382 A | * | 11/1989 | Moret et al. | ................. 433/118 |
| 5,421,726 A | * | 6/1995 | Okada | ..................... 15/22.1 X |
| 5,471,695 A | * | 12/1995 | Aiyar | ........................... 15/22.1 |
| 5,947,912 A | * | 9/1999 | Montagnino | ............ 606/161 X |
| 5,987,681 A | * | 11/1999 | Hahn et al. | ................... 15/22.1 |

FOREIGN PATENT DOCUMENTS

| | | |
|---|---|---|
| DE | 1 212 036 | 3/1966 |
| DE | 197 45 876 | 4/1999 |
| EP | 655 209 | 5/1995 |
| EP | 850 602 | 7/1997 |
| WO | 98/36703 | 8/1998 |

* cited by examiner

Primary Examiner—Mark Spisich
(74) Attorney, Agent, or Firm—Ostrolenk, Faber, Gerb & Soffen, LLP.

(57) ABSTRACT

An accessory mount for an electric toothbrush having a motor which is arranged in a handpiece for driving vibration-generating mechanism. The mount including an elongate protective cover attachable to the handpiece. The vibration-generating mechanism is arrangeable in an interior of the elongate protective cover. A sleeve is fitted onto the protective cover so as to cover the protective cover over at least part of its length.

14 Claims, 4 Drawing Sheets

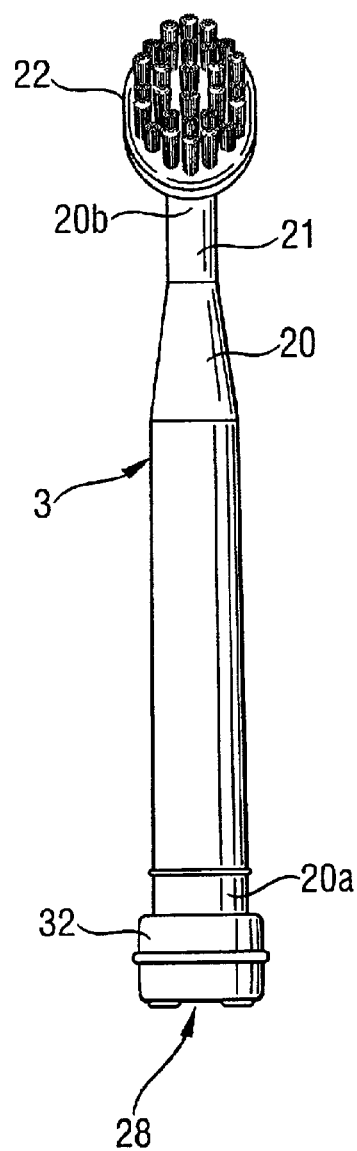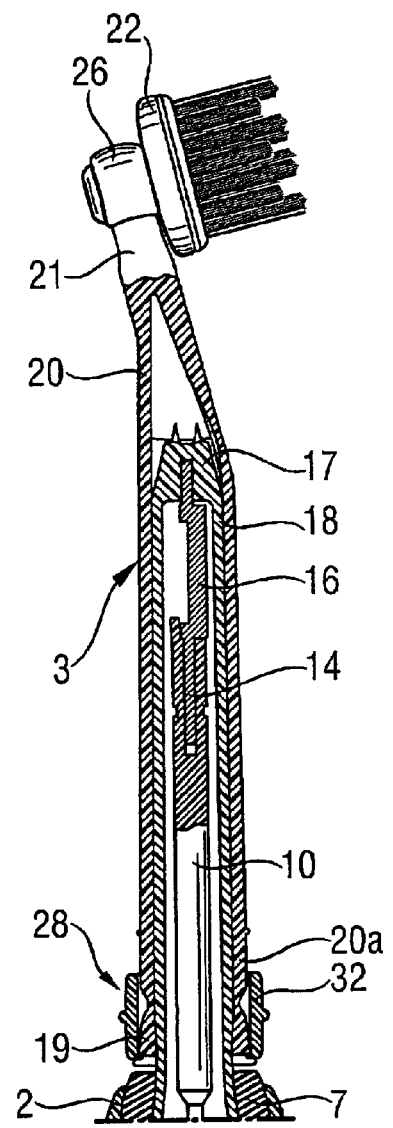

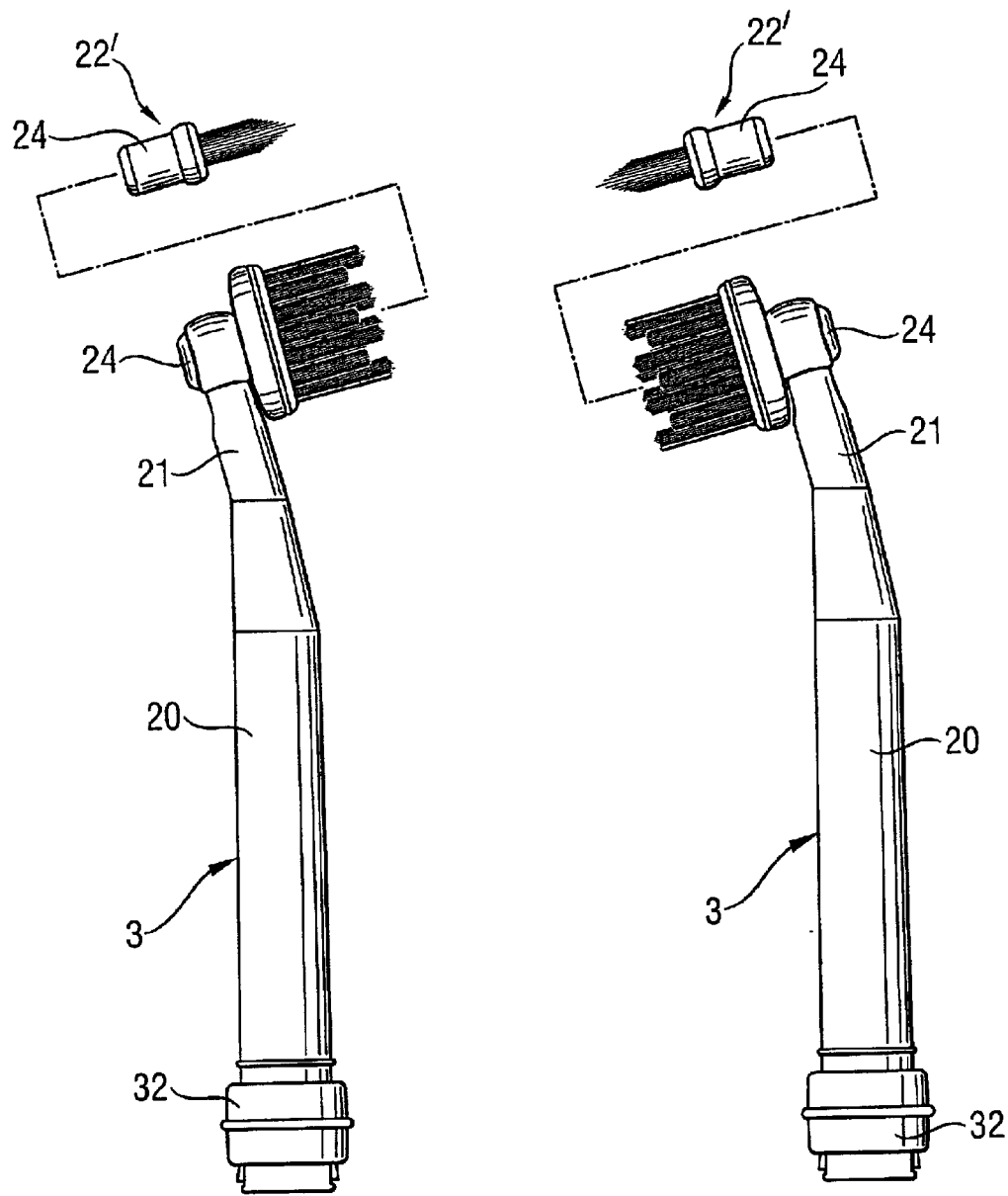

ACCESSORIES MOUNT FOR AN ELECTRIC TOOTHBRUSH

BACKGROUND OF THE INVENTION

1. Field of the Invention

The invention relates to a mechanically driven device for cleaning the oral cavity, in particular an electric toothbrush, and to an accessories mount for a device of this type.

2. Discussion of the Prior Art

Electric toothbrushes generally comprise a handpiece, in which the electric drive means are accommodated, a brush head and a spindle which connects the handpiece to the brush head.

An electric toothbrush of this generic type is known from European reference EP 0 850 602, which was filed,in the name of the present applicant. This toothbrush essentially comprises a handpiece, a brush head, a pin which connects the handpiece to the brush head and a motor which is arranged in the handpiece and sets an unbalanced mass in rotation. The unbalanced mass is arranged in the vicinity of the brush head and is set in rotation by an elongate pin which is coupled to the output spindle of the drive motor. The housing part which bears the drive means is attached to the handpiece via damping means in order to prevent vibrations in the handpiece. During use, the rotary movement of the unbalanced mass generates a centrifugal force which in turn, in the brush head, generates vibrations which are damped in the handpiece.

This device comprises a brush which is arranged at the end of the brush head in order to clean the oral cavity. Although the way in which it functions is satisfactory, the used brushes cannot be replaced since they remain fixedly connected to the device.

Toothbrushes are already known from the prior art. According to some proposals, the brushes are removably attached to the end of the brush head, while according to other proposals they are connected to a mount which is arranged removably on the pin which connects the brush to the drive mechanism. In both cases, there are sealing problems, since the water and toothpaste can penetrate into the interior of the device; for design reasons, the attachment parts are connected to drive parts of the toothbrush which are arranged in the interior. In addition, only the brush is exchanged, while its mount remains attached to the device, and for this reason hygiene requirements are no longer satisfied if it is intended for the device to be used by another person as well.

SUMMARY OF THE INVENTION

Therefore, one object of the invention is to eliminate the above-mentioned drawbacks and to provide an electric toothbrush which is fitted with an accessories mount, in which the used brushes can be replaced easily and in which the required hygiene conditions are satisfied in the event of use by different people.

Another object of the invention is to provide an accessories mount for electric toothbrushes to which different accessories for cleaning the oral cavity can be removably and therefore exchangeably attached.

A further object of the invention is to provide an accessories mount of simple structure for electric toothbrushes, which is easy to fit to the device and to remove again from the device, which functions reliably and which can be manufactured as a mass-produced item at the lowest possible price.

According to the invention, these objects are achieved by means of an accessories mount for electric toothbrushes which is equipped with a motor arranged in the handpiece for driving the means which generate the vibrations in the brush head. The means which generate the vibrations are arranged in the interior of an elongate protective cover which is attached to the handpiece. The accessories mount comprises a sleeve which is fitted onto the protective cover and covers the latter over at least part of its length.

The means which generate the vibrations in the brush head, in particular the unbalanced mass and the spindle which sets the unbalanced mass in rotation, are arranged in the interior of the elongate protective cover, one end of which is fixedly connected to the handpiece of the device and the other end of which is arranged freely. The protective cover is designed as a closed part for sealing reasons. In addition, the accessories which are provided for cleaning the oral cavity are held by an accessories mount which is substantially formed by a sleeve surrounding the protective cover.

This has the advantage that all the components of the vibration mechanism are arranged in a hidden and encapsulated position and therefore do not come into contact with the fingers of the user. A protective cover of this type made from plastic also provides additional protection for people who are sensitive to metal. In addition, this solution ensures that there is a good seal against water and toothpaste, since the protective cover is designed as a closed part.

Another advantage is that each user has his own accessories mount, the length of the sleeve corresponding to the length of introduction into the oral cavity. As a result of the user changing the sleeve, at the same time the accessory is changed and therefore the outer surface of the protective cover which supports the sleeve remains clean.

The sleeve advantageously covers the protective cover over its entire length which projects beyond the handpiece.

The protective cover is thus protected by the appropriate sleeve which has been fitted during use over its entire length and is not exposed to contamination by cleaning liquid flowing along the sleeve.

The bottom end of the protective sleeve is advantageously connected to the handpiece by means of an elastic ring.

In an electric toothbrush as described in EP 0 805 602 which has been filed in the name of the applicant, the unbalanced mass is advantageously arranged in the vicinity of the brush head. The unbalanced mass is advantageously set in rotation by an elongate spindle, and the driving force of the motor is transmitted to the spindle via a flexible coupling arranged in the vicinity of the brush head. The fact that the rotation point is at a distance from the load point, in particular from the center of gravity of the unbalanced mass, increases the amplitude of the vibrations. The elastic ring which connects the end of the protective cover to the handpiece ensures that the vibrations are magnified in the brush head and are attenuated in the handpiece.

Preferably, the sleeve at its one end has attachment means for releasable attachment to the protective sleeve and, at its other, opposite end, has holding means for the accessories provided for cleaning the oral cavity.

The means for attaching and locking the sleeve on the protective cover are provided at a distance from the region which receives the toothpaste, so that the toothpaste cannot contaminate the locking mechanism and no functional problems occur.

The end of the sleeve which bears the accessories is advantageously oriented obliquely with respect to the longitudinal axis of the sleeve.

This configuration offers the advantage that the brush can be passed to the mouth in an ergonomic way, depending on the way it is handled by the user, but the mechanism accommodated in the protective cover remains aligned in a straight position. In addition, this obliquely oriented configuration exhibits good mechanical strength.

The angle between the end region of the sleeve and its longitudinal axis is advantageously between 8° and 20°, preferably 15°. It has been found that an optimum ergonomic design is achieved with an angle of inclination of this magnitude.

The means for holding the accessories are advantageously formed by a part which has an opening for receiving the accessories.

It is thus possible to insert various types of exchangeable accessories which have pegs with a suitable cross-sectional shape into the mount, with the accessories, in the most simple design in particular, being pressed into the receiving opening. The clear width of the receiving opening is advantageously of polygonal, preferably square design.

This has the advantage of providing a simple and reliable holding and locking means, the peg of the accessory being clamped into the receiving opening.

The receiving opening is preferably of continuous design.

In this way, it is possible for the accessory to be attached to one side or the other of the accessories mount, as desired.

According to a preferred embodiment of the invention, the accessory is formed by an oval brush. A brush of this type can be guided to the teeth in such a way that its larger diameter is oriented either parallel or perpendicular to the row of teeth, depending on the intended purpose, in particular that of cleaning the teeth, massaging the gums, etc.

According to another embodiment of the invention, the accessory is formed by a rotary piece with a conical tip. Such an accessory can be used in conjunction with an accessories mount according to the invention, preferably for cleaning the interdental spaces and the gum line.

According to another embodiment of the invention, the accessory may be formed by dental floss which is secured in a holder.

It is also possible for a dental-floss holder to be fitted to an accessories mount according to the invention, in which case the dental floss is arranged in a fixed position in the holder but it is possible to exchange the dental-floss holder or to attach it in an inclined position on one or the other side of the accessories mount.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

FIG. 2 shows a front view of an accessories mount according to the invention;

FIG. 3 shows a section on line A—A from FIG. 1, through an accessories mount which is fitted on the toothbrush head;

FIGS. 4a and 4b show different arrangements of accessories and a plurality of individual accessories which can be used with the accessories mount according to the invention;

DETAILED DESCRIPTION OF THE PREFERRED EMBODIMENTS

Figure 1:
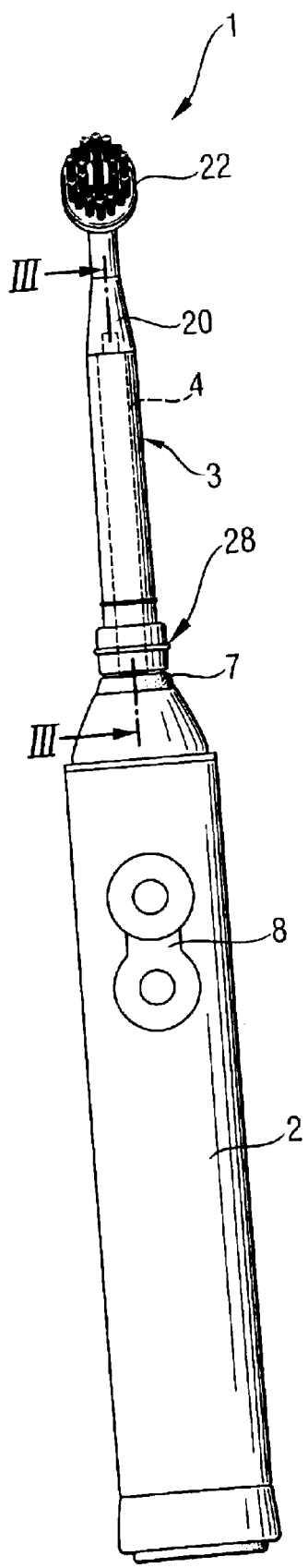
FIG. 1 shows a front view of an electric toothbrush with an accessories mount according to the invention.

The electric toothbrush 1 illustrated in FIG. 1 comprises a handpiece 2 and a brush head 4, onto which an accessories mount 3 according to the invention has been fitted. The handpiece 2 accommodates an electric motor and a flexible connecting piece which connects the motor spindle to the brush head spindle 10.

The brush head spindle 10 is formed by an elongate pin, in which the bottom end of the spindle 14 of an unbalanced mass 16 is secured. The top end of the spindle 14 is fitted into a corresponding opening in an elongate protective cover 18. The brush head spindle 10 is made in by particular from plastic, while the spindle 14 and the unbalanced mass 16 are made from metal. The unbalanced mass 16 is advantageously semicircular in cross section, the center of the semicircle lying on the spindle 14. At its two ends, the spindle of the unbalanced mass 16 is secured removably with respect to the adjacent parts. However, it is also possible to provide a fixed holder or for the pin 10, the unbalanced-mass spindle 14 and the unbalanced mass 16 to be designed as a single part.

The cover 18 on one side bears the spindle 14 of the unbalanced mass 16, the pin 10 setting the unbalanced mass 16 in rotation. On the other side, the cover 18 contains all the components so as to seal them in. The protective cover 18 is fixed into the handpiece 2, the elastic sealing ring 7 ensuring a seal. This allows the electric toothbrush to be of compact and sealed design.

The accessories mount 3 according to the invention is fitted onto the protective cover 18 and connected to the latter via attachment means 28 on the brush head 4. The accessories mount 3 comprises a sleeve 20, the top end 20b of which is equipped with means 26 for holding the accessories which are required to clean the oral cavity and the bottom end of 20a which is equipped with the attachment means 28 for attaching it to the cover 18 or the toothbrush head 4.

To ensure a firm and rotationally secure connection between the sleeve 20 which bears the accessory and the protective cover 18, the protective cover 18 has a flattened top end 17 on one side, which interacts with a corresponding opening in the interior of the sleeve 20 of the accessories mount 3. On the other side, the protective cover 18 has a bottom end which is provided with two cutouts 19.

The means 28 for attaching the sleeve 20 to the protective cover 18 comprise, as can be seen from FIG. 3, a slide ring 32 which can slide along the bottom end of the sleeve 20 and is provided with two elastic tongues. The slide ring 32 is arranged in such a way that it is guided displaceably between two limit stops. The bottom limit stop corresponds to the locking position, in which the sleeve 20 is fixed on the protective cover 18. The top limit stop corresponds to the open position, in which the sleeve 20 can be removed from the protective cover 18.

The top end 20b of the sleeve 20 which forms the accessories mount 3 advantageously comprises an obliquely oriented section 21 with the holding means 26 arranged in its end region for various accessories 22, 22' for cleaning the oral cavity. The angle of inclination of the section 21 is 8° to 20°, advantageously 15°, so that the accessories mount 3 is oriented obliquely forward or backward and the corresponding accessory 22 can thus be introduced into the mouth at an angle.

Figure 5:
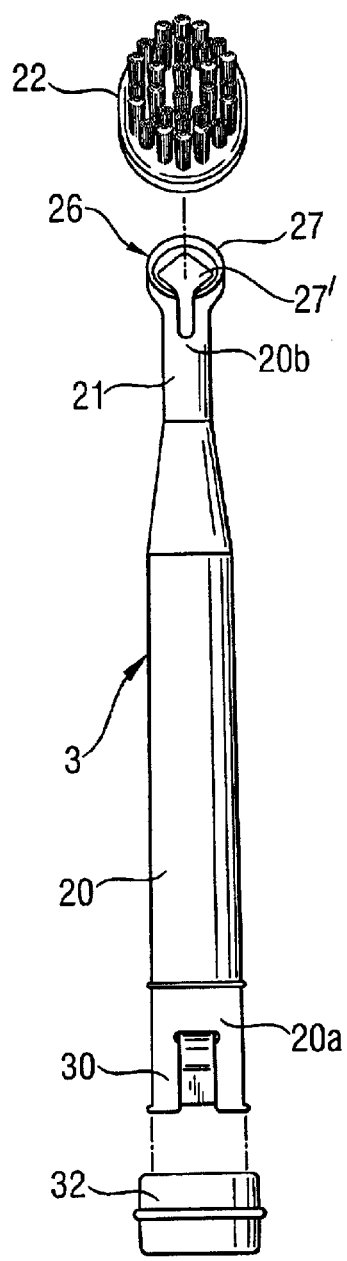
FIG. 5 shows an exploded view of the various components of an accessories mount according to the invention.

As can be seen from FIG. 5, the attachment means 26 are formed by a part 27 which is connected to the end section 21 of the sleeve 20. The part 27 may be of removable design and provided with attachment means for attaching it to the sleeve 20. However, the part 27 is advantageously formed integrally with the sleeve 20. The part 27 has a continuous receiving opening 27' into which the accessories 22, 22' are fitted.

The opening 27' is preferably of square design, but can alternatively be of any other polygonal or even, in extremis, circular shape. The accessory 22, 22' which is fitted into the opening 27' has a peg or pin 24 which matches the shape of the opening 27'. The accessories 22, 22' are removably attached to the sleeve 20, in particular by being clamped, being pressed in, by elastic means, by screw connection or by equivalent attachment means. Preferably, the accessories are attached by being clamped in an elastic holder.

All the components of the accessories mount 3, in particular the sleeve 20, the slide ring 32 and the accessories which are attached in the accessories mount 3 are advantageously made from plastic, which is beneficial for people who are allergic to metallic materials and allows mass production at low prices.

During use, an accessory 22 or 22' is fitted into the sleeve end 21, then the sleeve 20 is fitted onto the protective cover 18, and the slide tube 32 is moved downward in order to lock the sleeve (20) on the brush head 4. By pressing the on-off switch 8, the electric motor which sets the spindle 10 and the unbalanced mass 16 in rotation is turned on. The spindle 10 is set in rotation via a flexible coupling arranged in the interior of the handpiece 2, so that vibrations occur around a rotation point located in the handpiece 2, and these vibrations are amplified because of the distance from the center of gravity of the unbalanced mass 16. Due to the elastic sealing ring 7, the vibrations maintain their amplitude in the brush head and are attenuated in the handpiece 2.

The rotary movement of the unbalanced mass 16 generates the vibrations in the brush head 4, the vibrations being transmitted to the accessory 22, 22' which is attached to the top end of the accessories mount 3. The vibrating accessory comes into contact with the teeth and/or the gums in order to clean the teeth and massage the gums.

As can be seen from FIGS. 4a and 4b, the accessories attached to the accessories mount may be toothbrushes of various forms, in particular oval 22 or conical 22' brushes which are used in particular to clean and care for the interdental spaces. It is also possible to use other accessories, for example dental floss which is secured in a holder which can be removed from the accessories mount 3.

Figure 6A:
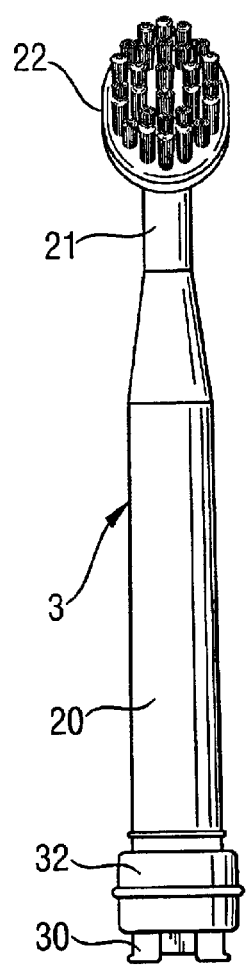
FIGS. 6a and 6b show embodiments of an accessories mount according to the invention, with an oval brush in two different positions on the accessories mount.
Figure 6B:
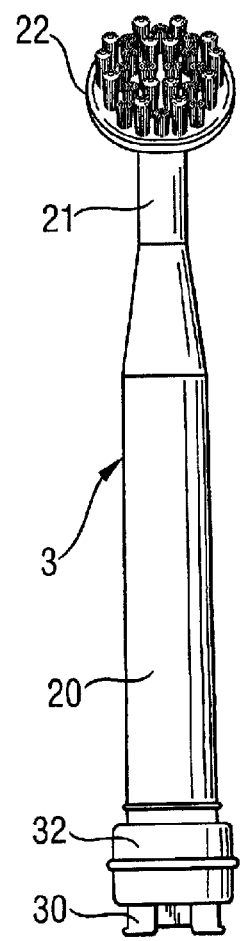

FIGS. 6a and 6b show the way in which an accessories mount 3 according to the invention is used with an oval brush 22. The part which serves as holding means 26 comprises, as can be seen from FIG. 5, a square attachment opening 27'. Since the peg 24 of the brush 22 is square in cross section, there are two different options for attaching the oval brush 22 to the accessories mount 3. Either the brush 22 is fitted on in such a way that its larger diameter is oriented parallel to the row of teeth (FIG. 6a) or the brush is rotated through 90° with respect to the first position (FIG. 6b). Since the receiving opening 27' is of continuous design, the sleeve 20 has an obliquely oriented section 21 and can be attached to the cover 18 in two different orientations rotated through 180°, it is thus possible for an oval brush to assume eight different positions on the accessories mount.

Further improvements can be made within the scope of the invention. For example, it is possible to provide an uncoupling device which separates the brush from the holder if an excessive pressure is exerted on the brush. The brush is attached to a seat by means of a spring arranged in its holder, the holder being arranged in the accessories mount according to the invention. In the event of a defined pressure being exceeded, the brush would be separated from its seat, so that it is no longer connected to the vibration means.

It is also possible to provide an accessories mount 3 with slide rings of different colors in order to identify the accessories mount as a function of a specific use.

The invention is not limited by the embodiments described above which are presented as examples only but can be modified in various ways within the scope of protection defined by the appended patent claims.

We claim:

1. An accessory mount for an electric toothbrush having a motor which is arranged completely within a handpiece for driving vibration-generating means that extends from the handpiece, comprising: an elongate protective cover attachable to the handpiece and configured so as to have an elongate portion exterior the handpiece and so that the vibration-generating means are arrangeable in an interior of the elongate protective cover; and a sleeve fitted onto the protective cover so as to cover the protective cover over at least part of its length, a dental accessory being mounted to the sleeve.

2. An accessory mount as defined in claim 1, wherein the sleeve covers the protective cover over substantially its entire length.

3. An accessory mount as defined in claim 1, and further comprising an elastic ring arranged to connect a bottom end of the protective cover to the handpiece.

4. An accessory mount as defined in claim 1, wherein the dental accessory is an accessory for cleaning an oral cavity, and further comprising attachment means at one end of the sleeve for removably attaching the sleeve to the protective cover, and-holding means at an opposite end of the sleeve for holding the accessory for cleaning an oral cavity.

5. An accessory mount as defined in claim 4, wherein the opposite end of the sleeve is oriented obliquely with respect to a longitudinal axis of the sleeve.

6. An accessory mount as defined in claim 5, wherein the angle between an end region of the sleeve and the longitudinal axis is 8° to 20°.

7. An accessory mount as defined in claim 4, wherein the holding means includes a part which has a receiving opening for accommodating the accessories.

8. An accessory mount as defined in claim 7, wherein the receiving opening has a polygonal shape.

9. An accessory mount as defined in claim 8, wherein the opening is square.

10. An accessory mount as defined in claim 7, wherein the receiving opening has an uninterrupted perimeter.

11. An accessory mount as defined in claim 4, wherein the accessory is an oval brush.

12. An accessory mount as defined in claim 4, wherein the accessory is formed by a rotatable piece with a conical tip.

13. An accessory mount as defined in claim 4, wherein the accessory is a holder in which dental floss is secured.

14. An electric toothbrush comprising: a hand piece; vibration-generating means that extend from the handpiece; a motor arranged completely within the handpiece for driving the vibration generating means; and an accessory mount having an elongate protective cover releaseably attached to the handpiece so as to have an elongate portion exterior the handpiece and, the vibration generating means being arranged in an interior of the elongate protective cover, and a sleeve fitted onto the protective cover, so as to cover the protective cover over at least part of its length, a dental accessory being mounted to the sleeve.

* * * * *